(12) United States Patent
Scussel

(10) Patent No.: US 7,927,378 B2
(45) Date of Patent: Apr. 19, 2011

(54) VACUUM ASSISTED PROSTHETIC SLEEVE AND SOCKET

(75) Inventor: Rick C. Scussel, Newton, AL (US)

(73) Assignee: Scussel SBJ Systems, LLC, Dothan, AL (US)

( * ) Notice: Subject to any disclaimer, the term of this patent is extended or adjusted under 35 U.S.C. 154(b) by 549 days.

(21) Appl. No.: 11/762,306

(22) Filed: Jun. 13, 2007

(65) Prior Publication Data

US 2008/0221705 A1 Sep. 11, 2008

Related U.S. Application Data

(60) Provisional application No. 60/904,833, filed on Mar. 5, 2007.

(51) Int. Cl.
*A61F 2/60* (2006.01)
*A61F 2/80* (2006.01)
*A61F 2/78* (2006.01)

(52) U.S. Cl. ............................... 623/36; 623/32; 623/33

(58) Field of Classification Search ...................... 623/32
See application file for complete search history.

(56) References Cited

U.S. PATENT DOCUMENTS

| | | | |
|---|---|---|---|
| 2,002,064 A * | 5/1935 | Kohl | 623/36 |
| 4,863,201 A | 9/1989 | Carstens | |
| 4,923,474 A | 5/1990 | Klasson et al. | |
| 5,258,037 A | 11/1993 | Caspers | |
| 5,376,132 A | 12/1994 | Caspers | |
| 5,534,034 A * | 7/1996 | Caspers | 623/32 |
| 5,549,709 A * | 8/1996 | Caspers | 623/24 |
| 5,571,208 A | 11/1996 | Caspers | |
| 5,735,906 A | 4/1998 | Caspers | |
| 5,904,722 A * | 5/1999 | Caspers | 623/34 |
| D429,335 S | 8/2000 | Caspers | |
| 6,508,842 B1 | 1/2003 | Caspers | |
| 6,554,868 B1 * | 4/2003 | Caspers | 623/34 |
| 6,645,253 B2 | 11/2003 | Caspers | |
| 6,726,726 B2 | 4/2004 | Caspers | |
| 6,761,742 B2 | 7/2004 | Caspers | |
| 6,926,742 B2 | 8/2005 | Caspers | |
| 6,974,484 B2 * | 12/2005 | Caspers | 623/34 |
| 7,025,793 B2 | 4/2006 | Egilsson | |
| 7,144,429 B2 | 12/2006 | Carstens | |
| 7,150,762 B2 | 12/2006 | Caspers | |
| 7,169,188 B2 | 1/2007 | Carstens | |
| 7,235,108 B2 | 6/2007 | Carstens | |
| 2004/0143345 A1 | 7/2004 | Caspers | |
| 2009/0036999 A1 * | 2/2009 | Egilsson et al. | 623/36 |
| 2010/0070051 A1 * | 3/2010 | Carstens | 623/34 |

* cited by examiner

*Primary Examiner* — David Isabella
*Assistant Examiner* — Jacqueline Woznicki
(74) *Attorney, Agent, or Firm* — Russell Carter Gaché; Maynard Cooper & Gale, PC

(57) ABSTRACT

A prosthetic sleeve and socket system, the sleeve including a flap or skirt concentrically arranged about the sleeve and configured to form a sealed chamber between the sleeve and socket when the sleeve is inserted into the socket. An air permeable material is interposed between the skirt and the sleeve to maintain a continuous interconnected air layer therebetween. An expulsion valve is provided to allow air contained within the sealed chamber to be forced out of the chamber ahead of the sleeve when it is inserted into the socket. A powered vacuum pump is also provided for producing and maintaining a partial vacuum in the sealed chamber for keeping the socket and sleeve joined. The system allows for a substantial reduction in size of known sockets and permits, in some instances, the disposal of bulky suspension straps currently in use to force the socket against a residual limb.

23 Claims, 7 Drawing Sheets

VACUUM ASSISTED PROSTHETIC SLEEVE AND SOCKET

This application claims the benefit of filing priority under 35 U.S.C. §119 and 37 C.F.R. §1.78 from U.S. Provisional Application Ser. No. 60/904,833 filed Feb. 5, 2007, for SCUSSEL/SBJ SUCTION LINER-SOCKET. All information disclosed in this prior application is incorporated herein by reference.

FIELD OF THE INVENTION

This invention relates to a prosthetic sleeve and socket combination, and more particularly, to a prosthetic sleeve having a flap or skirt concentrically arranged about the sleeve and configured to form a sealed chamber between the sleeve and socket when the sleeve is inserted into the socket.

BACKGROUND OF THE INVENTION

An amputee is a person who has lost part of an extremity or limb such as a leg or arm. That which remains is commonly referred to as a residual limb. Residual limbs come in various sizes and shapes with respect to the stump. For instance, new amputations are often slightly bulbous or cylindrical in shape while older amputations that have atrophied are generally more conical in shape. Residual limbs may also be characterized by their various individual configurations including the volume and shape of a stump, bony prominence, uneven limb volume or soft tissue configurations. For example, a leg severed above the knee generally terminates in a fleshy stump while a leg severed below the knee generally terminates in a bony stump.

More particularly, referring to FIG. 1, an above the knee residual limb 10 is shown and described as a leg 12 having been severed above the knee terminating in a stump 14. In this case stump 14 is formed by the femur 16 and the large muscles of the upper leg that surround femur 16. A below the knee residual limb 18 is shown in FIG. 2 and described as a leg 20 having been severed below the knee terminating in a stump 22. In this case stump 22 is formed by the severed tibia 28 and fibula 30 and the smaller, less voluminous muscles of the lower leg. Thus, a below the knee residual limb 18 has its stump 22 generally characterized as being a more bony structure while an above the knee residual limb 10 is characterized as including more soft tissue.

Artificial limbs typically used by a leg amputee have sockets to put the amputee's stump into. There are generally two categories of sockets. There are hard sockets wherein the stump goes right into the socket actually touching the socket wall without any type of liner or stump sock. Another category of sockets is a socket that utilizes a liner or insert. Both categories of sockets typically are opened ended sockets having a hollow chamber in the bottom.

In the past, most artificial limbs were suspended from the amputee's body by some form of pulley, belt or strap suspension often used with various harnesses, leather lacers or lacings. However, these types of suspension systems are bulky and uncomfortable to wear, and when the residual limb was a leg severed above the knee, the socket had to include an ischial flare which only increased bulk and discomfort. Another method of suspending artificial limbs required the amputee to use a latex rubber tube formed into a rubber-like sleeve which would be rolled on over both the top of the artificial limb and onto the amputee's thigh. In some instances, a negative pressure system was used in combination with the rubber sleeve which required forming a negative pressure chamber between the leg and socket using a vacuum pump. The sleeve acted as a seal between the limb and socket thereby suspending the socket from the limb. However, since the seal was formed on the outside of the socket it was prone to puncturing which resulted in suction loss within the sealed chamber and detachment of the socket from the residual limb.

SUMMARY OF THE INVENTION

The present invention is directed to a prosthetic sleeve and socket system, and more particularly, to a prosthetic sleeve having an additional sleeve or skirt concentrically arranged about the sleeve and configured to form a sealed chamber between the sleeve and socket when the sleeve is inserted into the socket. In addition, a method of attaching a prosthesis to a residual limb is presented consisting of placing a prosthetic sleeve about a residual limb, inserting the residual limb and prosthetic sleeve into a socket conforming to the shape of the residual limb, forming a continuous seal between the sleeve and an interior surface of the socket, evacuating air from a chamber contained between the residual limb and an interior surface of the socket and creating a partial vacuum within the chamber sufficient to maintain the socket coupled to and suspendable from the residual limb. The sleeve includes a continuous skirt about the sleeve that cooperates with the interior surface of the socket to form the seal, the sleeve forming a continuous connection along an upper margin of the skirt to the sleeve. The method farther includes pushing air from the chamber through an expulsion valve coupled to an opening in the socket by inserting the residual limb into the socket and simultaneously and continually pulling air from the chamber through a vacuum pump coupled to an opening in the socket. Preferably, the air contained between the sleeve and the skirt is removed by a "wicking" positioned there between. Suitable wicking can be an air permeable cotton sock fitted onto the residual limb over the sleeve.

DETAILED DESCRIPTION OF PRESENTLY PREFERRED EMBODIMENTS

Figure 1:
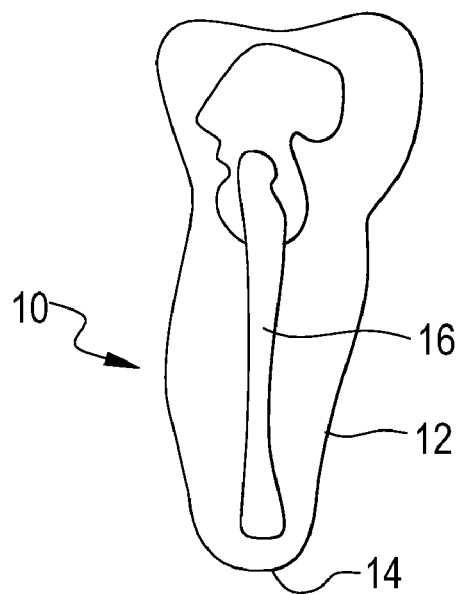
FIG. 1 is a side elevational view of the tissue and skeletal structure of an amputee's residual leg severed above the knee.
Figure 2:
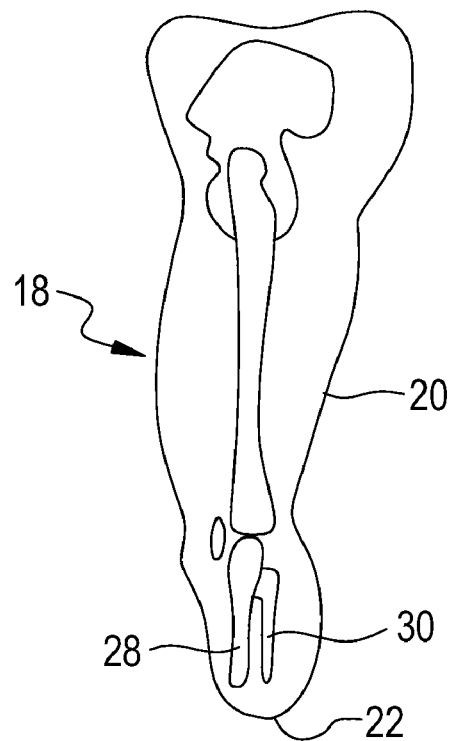
FIG. 2 is a side elevational view of the tissue and skeletal structure of an amputee's residual leg severed below the knee.
Figure 3:
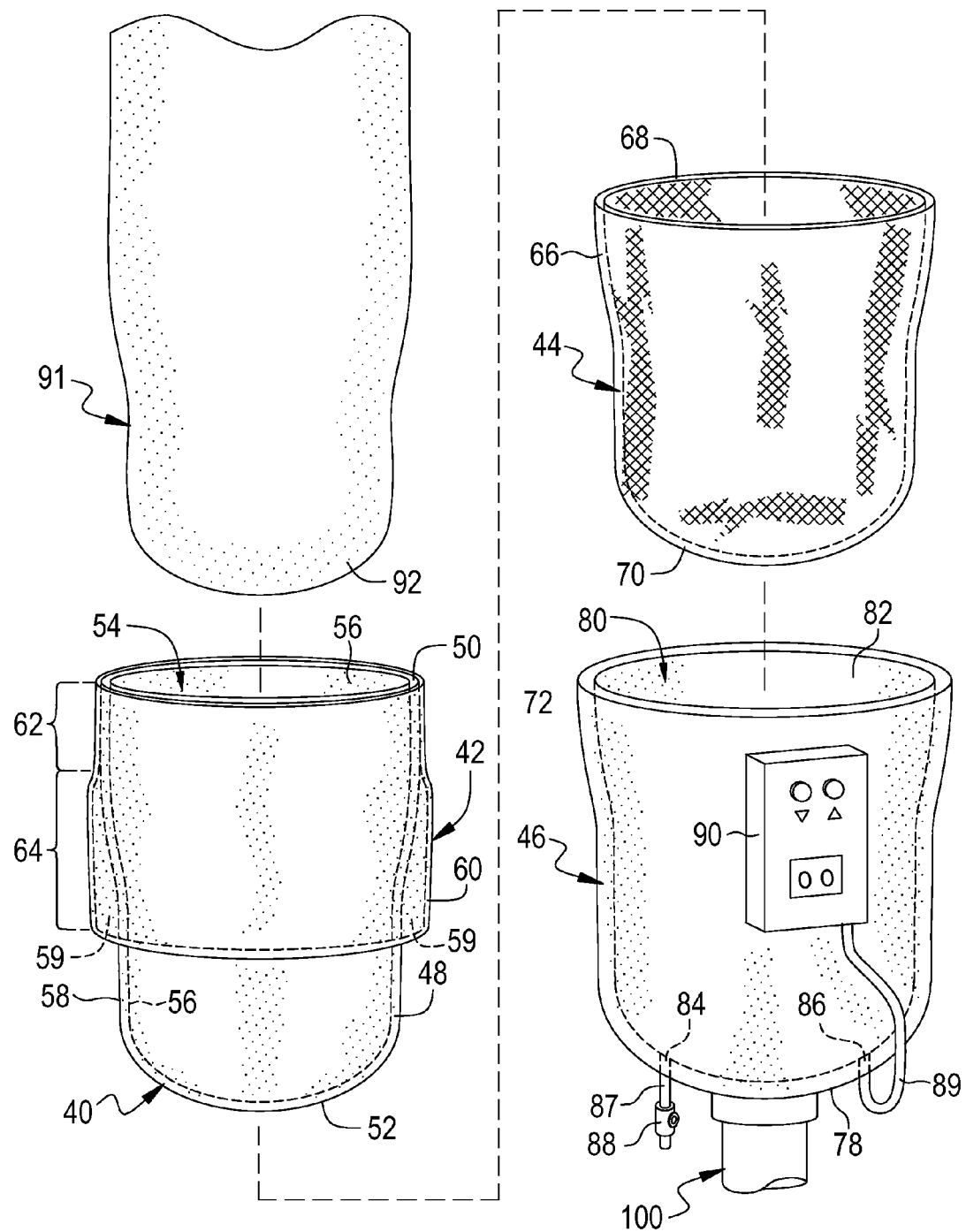
FIG. 3 is an exploded elevational view of a prosthetic sleeve and socket system in accordance with a preferred embodiment of the present invention.

FIGS. 1 and 2 illustrate an above the knee residual limb 10 and a below the knee residual limb 18, respectively. The present invention is illustrated in FIGS. 3 through 9, where like portions share like numbering. Generally, as illustrated in FIG. 3, the prosthetic sleeve and socket system of present invention includes a pliable, silicone sleeve 40 conformable to the shape of an amputee's residual limb, a pliable, continuous skirt or flap 42 concentrically arranged about sleeve 40, an air wick 44 and a prosthetic socket 46 conforming to the shape of the amputee's residual limb. "Air wick" is hereby defined as an air permeable material, said material including air permeation characteristics in all directions. For example, a cotton sock would be one form of an air wick.

Figure 4:
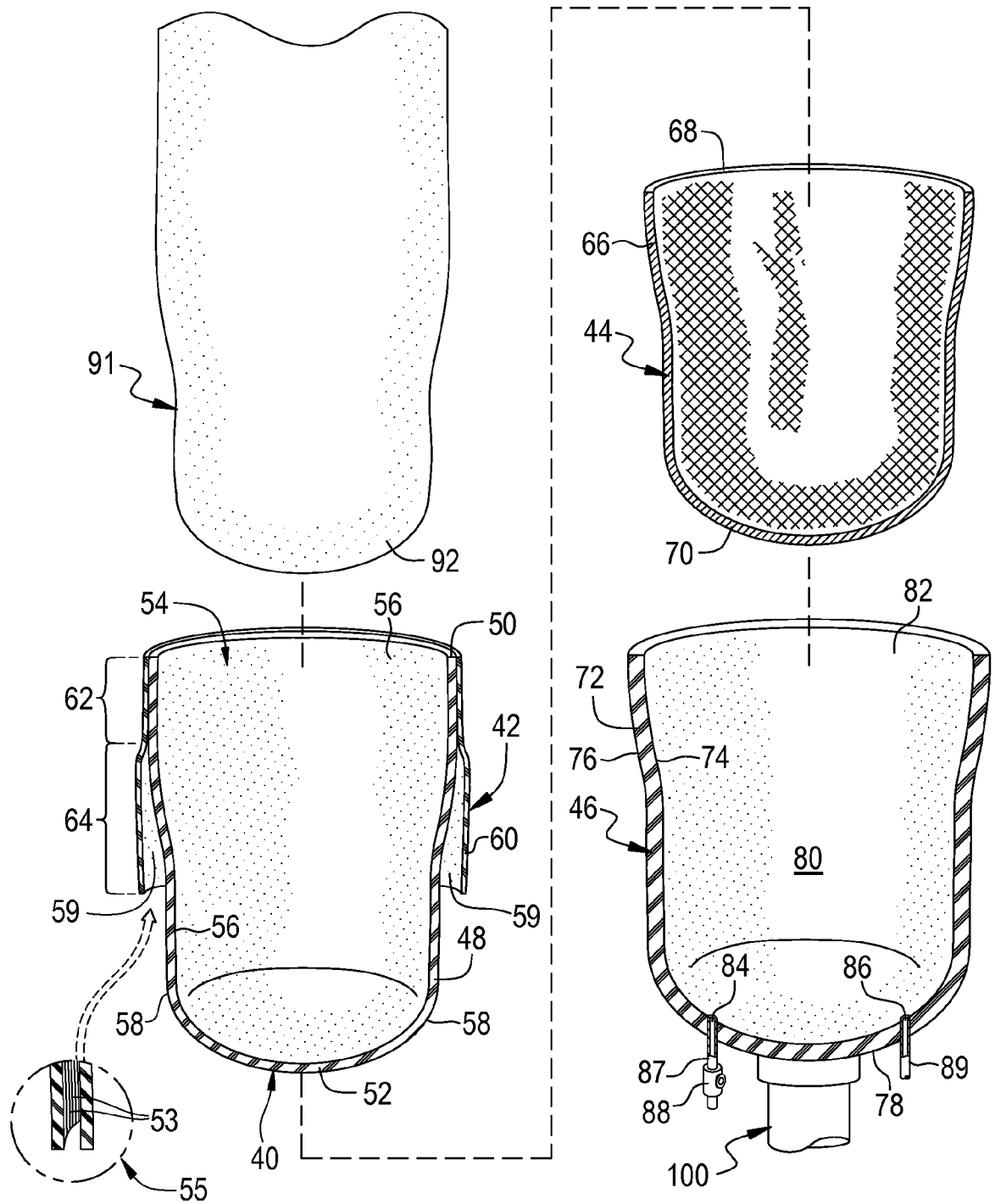
FIG. 4 is a cross-sectional view the prosthetic sleeve and socket system of FIG. 3.

Referring to FIG. 4, sleeve 40 includes a cylindrical, continuous sidewall 48 having an open top end 50 and a closed bottom end 52. A limb receiving compartment 54 defined by open top end 50 and an inner surface 56 of sleeve sidewall 48 and bottom end 52 are included in sleeve 40. Since sidewall 48 and closed bottom 52 are constructed of pliable, silicone sheeting, compartment 54 is sufficiently pliable to fit snuggly around an amputee's residual limb, whether it is an arm or a leg. Preferably, sleeve sidewall 48 has a uniform thickness of between 3 mm to 6 mm and has surface characteristics that lends itself to comfortably gripping a user's skin.

Skirt 42, which is positioned concentrically about sleeve 40, connects to and is integral with an outer surface 58 of sleeve sidewall 48. In particular, skirt 42 includes a substantially, rectangular silicone sheet 60 having an attached upper margin 62 and a free lower margin 64. Specifically, upper margin 62 is attached to sidewall 48 adjacent to open top end 50 and defines a continuous, circumferential envelope 59 between outer surface 58 and skirt 42. This can be accomplished using an adhesive or by stitching or producing sleeve 40 and skirt 42 as a single piece. As may be seen at inset 55, various features may be molded into the surface of either the sleeve or the skirt, such as vertical ridges 53 as shown, so that air readily passes between the skirt and sleeve to avoid the formation of air pockets. Preferably, upper margin 62 is attached to sidewall 48 with skirt 42 affixed directly on the outer surface 58 and extends downward in the general direction of closed bottom 52, but leaving envelope space 59 between the two. This way skirt 60 can be easily folded downward to lie against outer surface 58 of sidewall 48 without creating an otherwise bulky fold about upper margin 62. Preferably, skirt 42 has a uniform thickness of between 1 mm and 3 mm.

As may be understood, while margin 62 is shown to be affixed to sleeve 40 from its upper most extent, affixation margin 62 may be moved down sleeve 40 from its upper most extent to provide an additional upper margin area free of skirt 42. This additional free upper margin area may extend upwards over more of surface skin area of residual limb 91 to allow for additional contact and stability of sleeve 40 over limb 91. In this manner, various sizes and configurations of sleeve 40 may be manufactured to fit various sizes and shapes of residual limbs, including residual limbs on arms, legs, fingers, etc. Similarly, various sizes and shapes of sockets 46 cooperatively shaped with sleeves 40 could be utilized to accommodate various shapes and sizes of residual limbs.

Figure 5:
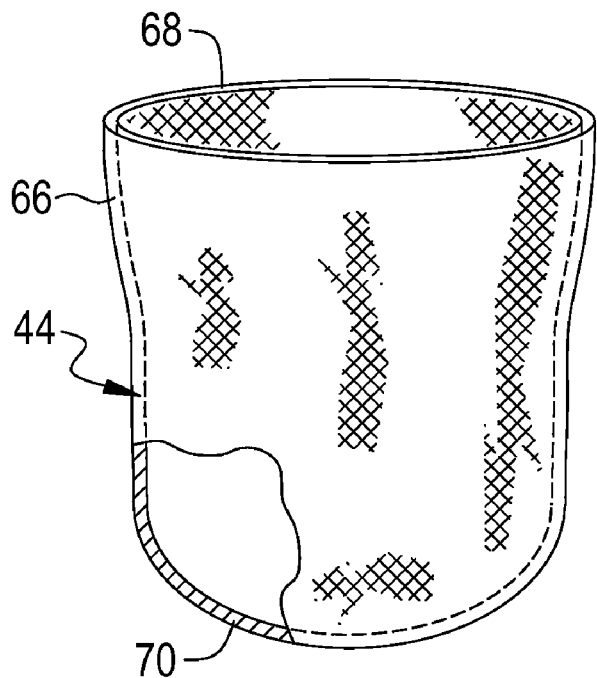
FIG. 5 is perspective view of an air wick in partial cross-section in accordance with the sleeve and socket system of FIG. 3.

Referring to FIG. 5, air wick 44 is constructed of a thin, air permeable fabric formed into a sock. Wick 44 therefore includes a cylindrical continuous wall 66, an open top 68 and a closed bottom 70. It is preferred that wall 66 has a height substantially equal to the distance between the point of upper attachment of margin 62 on skirt 42 downward to closed bottom end 52. This positions air wick 44 over bottom end 52 and sidewall 48 of sleeve 40, with wall 66 continuously extended between skirt 42 and outer surface 58 of sidewall 48 when skirt 42 is pressed against sleeve 40.

Figure 6:
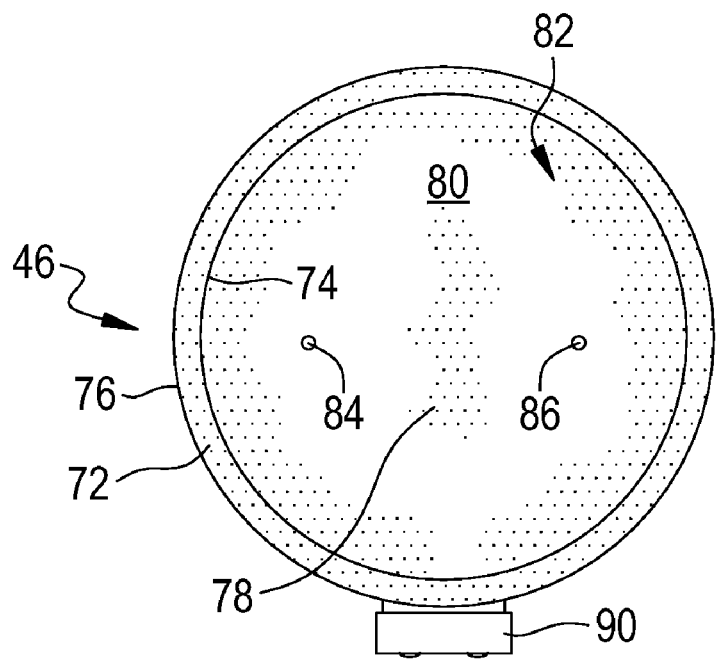
FIG. 6 is a plan view of the open end of the socket of FIG. 3.

Referring to FIG. 6, socket 46 is composed of a socket wall 72 having an interior surface 74 and an exterior surface 76 and a socket distal end 78. Socket distal end 78 merges integrally into socket wall 72 at the lower end of the wall. Jointly with the interior surface 74, distal end 78 forms a substantially cup-shaped inner volume 80 which is accessible through a proximal residual limb insertion opening 82 at the proximal end. Since socket 46 is configured to attach to an amputee's residual limb by a partial vacuum it is a so-called suction-socket.

A pair of openings 84 and 86 are formed through socket distal end 78 for allowing air within inner volume 80 to selectively escape from inner volume 80 ahead of an amputee's residual limb 91 when the latter is inserted into inner volume 80. In particular, opening 84 is coupled to a selectively actuated expulsion valve 88 for allowing air under pressure to exit inner volume 80 via short conduit 87. An example expulsion valve suitable for use in the herein described system is a V4 or V5 expulsion valve offered by Otto Bock HealthCare, Inc. Opening 86 is connected to a vacuum source 90 via line 89 for pulling air out of inner volume 80 to form a partial vacuum. Vacuum source 90 is preferably self-contained and includes a power source, a release valve, a vacuum pump and a pressure control means configured to maintain pressure within inner volume 80 at a predetermined pressure. An exemplary vacuum source includes the "eVAC" model no. DF-100 manufactured by Smith Global, located in Laurie, Mo.

Figure 7:
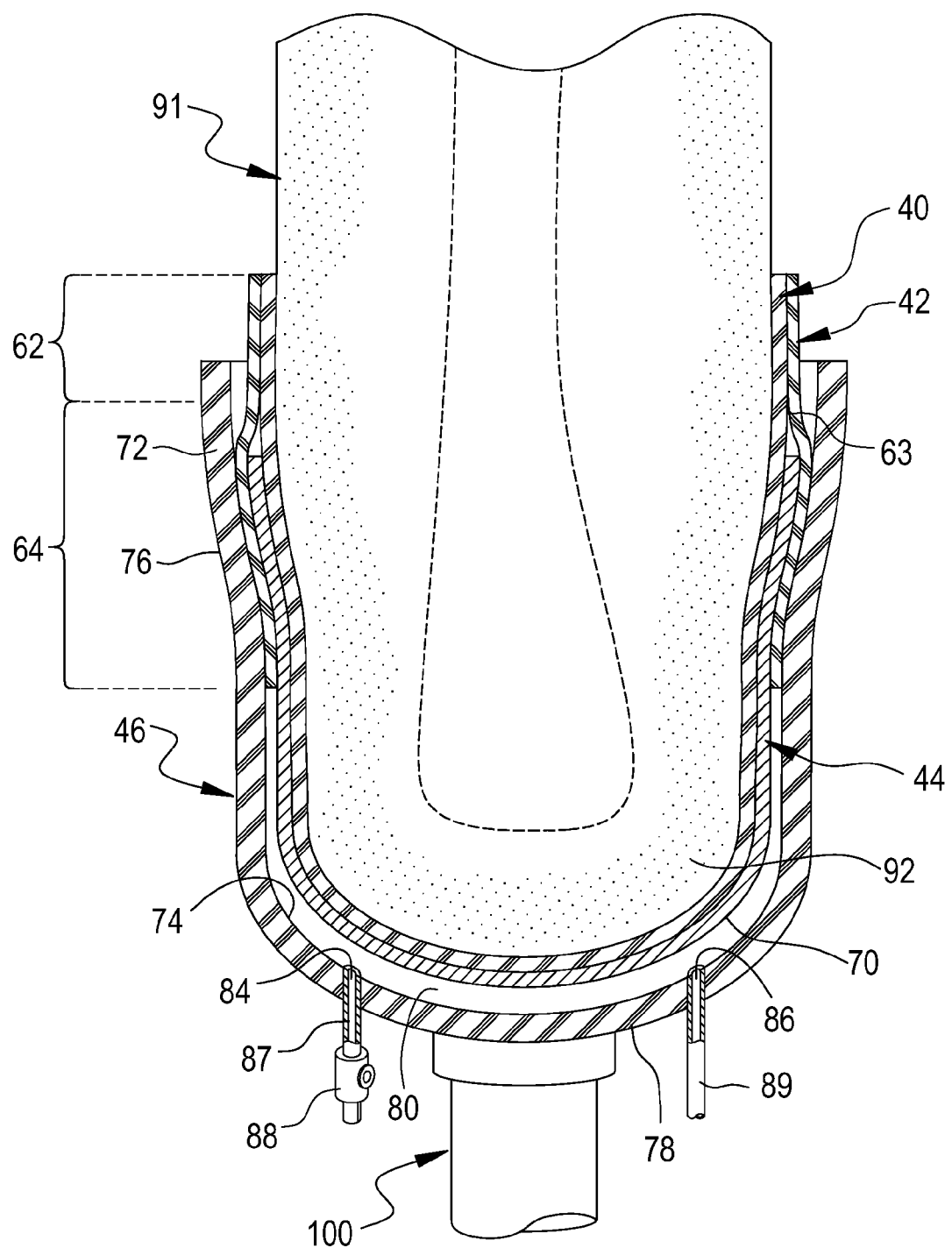
FIG. 7 is a cross-sectional view of the sleeve and socket system of FIG. 3 suspended from an amputee's residual leg above the knee.
Figure 8:
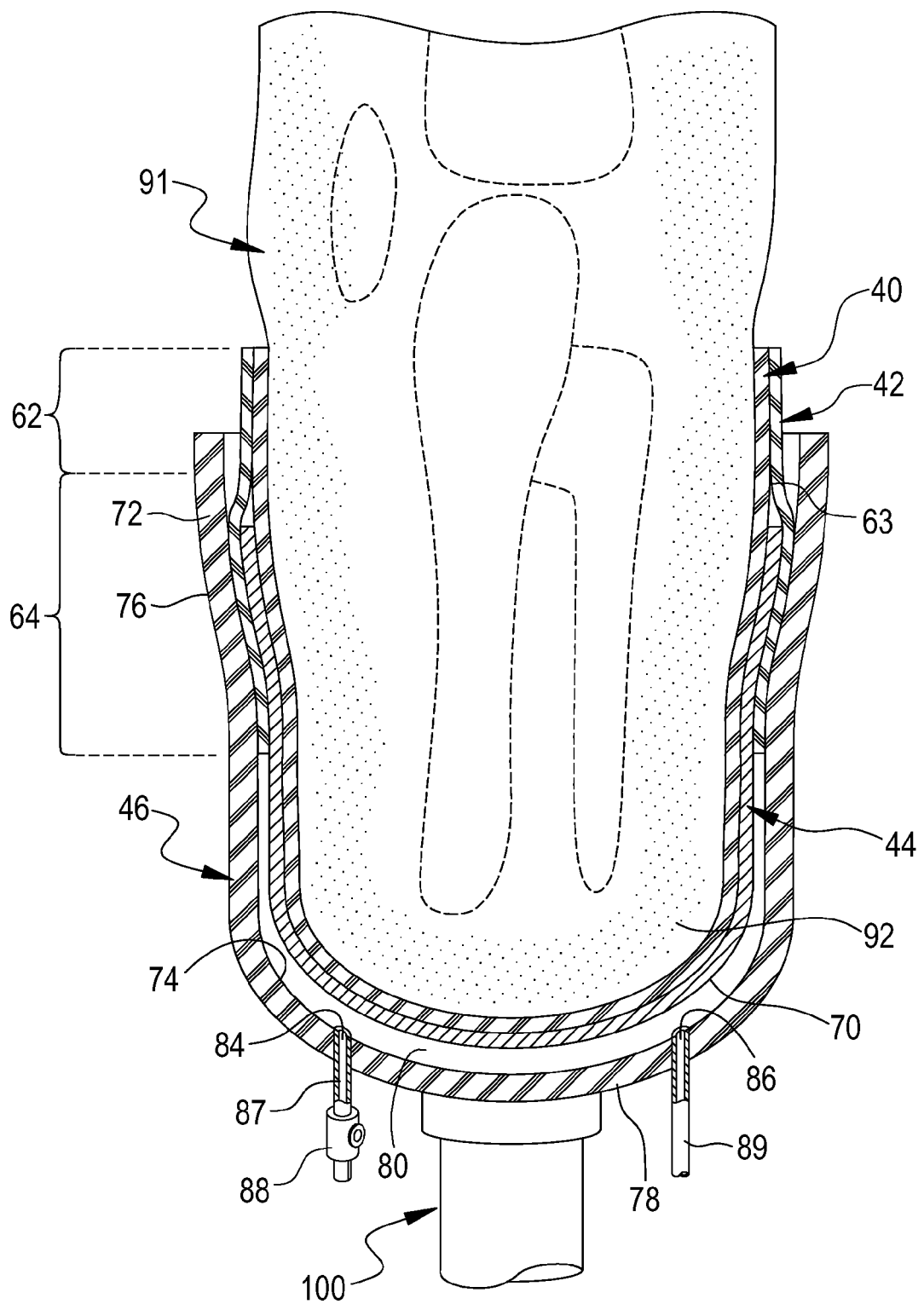
FIG. 8 is a cross-sectional view of the sleeve and socket system of FIG. 3 suspended from an amputee's residual leg below the knee; and, FIG. 9 is a cross-sectional view of the sleeve and socket system of FIG. 7 illustrating formation of a seal between the sleeve and socket.

Referring to FIGS. 7 and 8, there is shown the prosthetic sleeve and socket system of the present invention suspended from a leg severed above the knee and a leg severed below the knee, respectively. In each instance, the amputee's severed or residual limb 91 includes a lower end 92 that is inserted through open top end 50 and into limb receiving compartment 54 of sleeve 40. Lower end 92 of the amputee's limb is fully engaged with inner surface 56 of sleeve sidewall 48 and closed bottom end 52, with sidewall 48 exerting pressure against the leg sufficient to maintain sleeve 40 suspended from lower end 92 of the amputee's limb when sleeve 40 is coupled to socket 46 and the desired prosthetic appendage 100. The diameter and length of sleeve 40 are determined based upon the length and diameter of lower end 92 and the amount of flesh present about lower end 92. The amount of flesh present can also dictate the thickness of sleeve sidewall 48 since the abundance or lack of flesh can determine how well sleeve 40 engages and remains engaged with socket 46. For example, in those instances where sleeve 40 and socket 46 are to be coupled with a leg severed below the knee the thickness of sleeve sidewall 48 may be increased to make up for the lack of flesh typically found about that part of the leg. Alternatively, when sleeve 40 and socket 46 are to be placed on a leg severed above the knee, the thickness of sleeve sidewall 48 may be less since the upper leg typically includes a relatively substantial amount of flesh.

With sleeve 40 positioned on lower end of the residual limb 91, air wick 44 is then positioned over closed bottom end 52 of sleeve 40 with closed bottom 70 of wick 44 being located adjacent to and in contact with closed bottom end 52. Further, wick 44 extends upwardly along sleeve sidewall 48 to sleeve sidewall's lower point of attachment 63 with skirt 42. This way, when skirt 42 is manipulated to lie flat against outer surface 58 of sleeve sidewall 48, air wick 44 prevents most or all direct contact between the sidewall 48 and skirt 42.

Lower end of the amputee's residual leg 91, along with sleeve 40 and air wick 44, are positioned within inner volume 80 of socket 46. In particular, closed bottom 70 of wick 44, along with sleeve 40, is positioned immediately above distal end 78 of socket 46 with sleeve sidewall 48 being located substantially parallel to socket sidewall 72. Skirt 42 is manipulated to lie flat against and between interior surface 74 of socket 46 and air wick 44. The interaction of skirt 42 with interior surface 74 acts to create a continuous seal 94 between sleeve 40 and socket 46. Seal 94 therefore encloses inner volume 80 within socket 46, defining inner volume 80 by interior surface 74, skirt 42 and sleeve sidewall 48.

Figure 9:
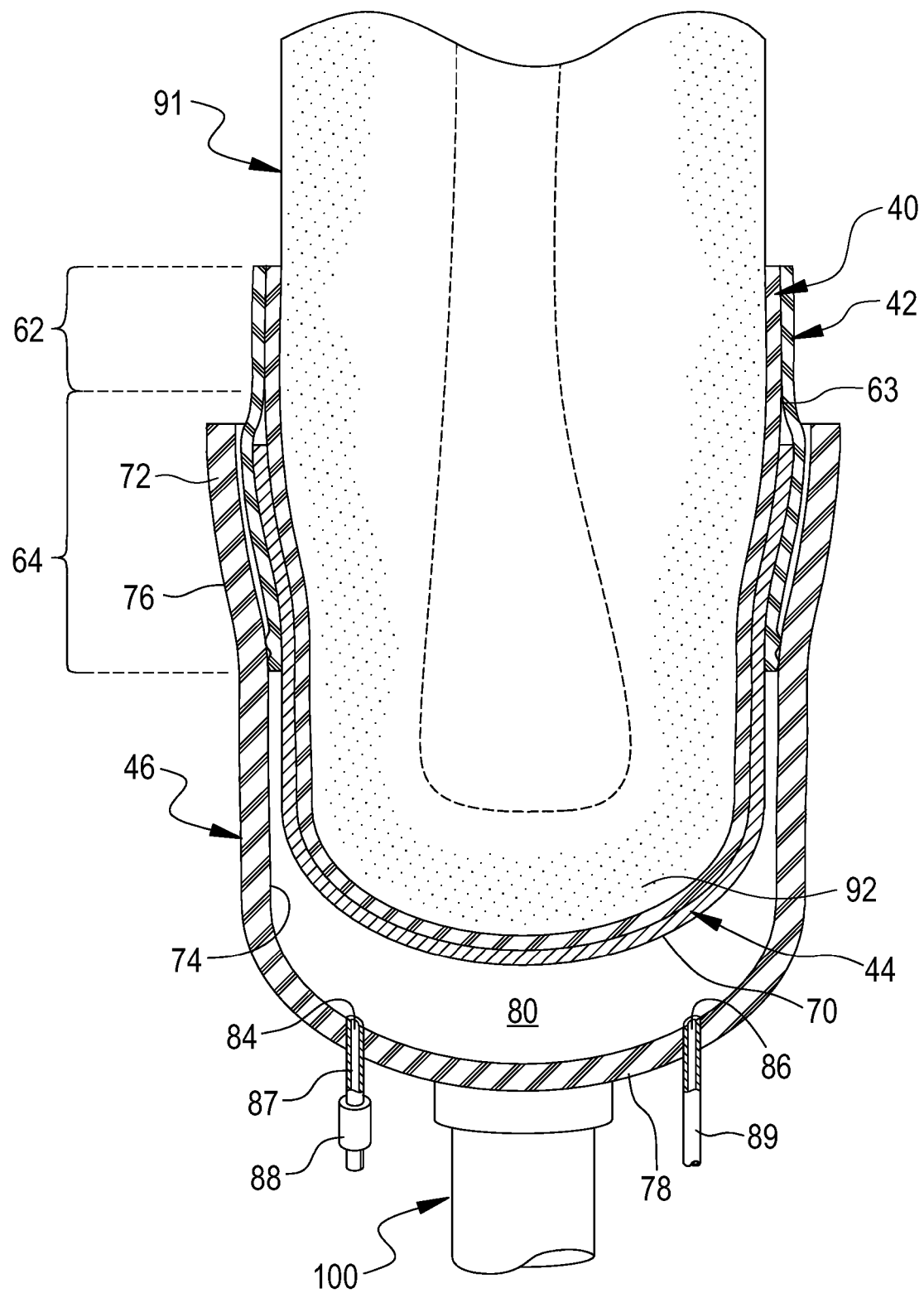

Referring to FIG. 9, seal 94 is first created when skirt 42 is initially inserted into inner volume 80. This occurs as soon as skirt 42 makes a continuous connection with interior surface 74 of socket 46. Thus, as sleeve 40 and skirt 42 are pressed into inner volume 80, seal 94 is created, maintained and moved downwardly toward distal end 78 thereby causing the air within socket 46 to be compressed. This further helps to press skirt 42 against interior surface 74 thus strengthening the interaction between skirt 42 and socket 46 and ultimately seal 94. Once the air reaches a predetermined pressure, the compressed air is allowed to escape from inner volume 80 through opening 84 and expulsion valve 88. Expulsion valve 88 typically includes a small manual release to control the timing and volume of air that might be expelled through it. Air can also escape through a release valve contained within vacuum source 90, if present, but vacuum source 90 itself will tend to evacuate the air held by seal 94 in response to and at a rate characterized by the operational specifications of the vacuum unit. By increasing the number of openings through which the compressed air can be selectively evacuated from inner volume 80, sleeve 40 is more easily inserted into and coupled with socket 46 since the compressed air can escape at a faster rate. Hence, it is anticipated that multiple expulsion orifices and vacuum conduit openings might be incorporated into the socket 46.

Once lower end 92 of the amputee's residual limb, along with sleeve 40 and air wick 44, are fully seated within inner volume 80 of socket 46, a partial vacuum is created within inner volume 80. In particular, vacuum source 90 acts to pull air within inner volume 80 out of socket 46 through opening 86 to create a regulated partial vacuum. Since air wick 44 is provided between skirt 42 and sleeve sidewall 48, the air located therebetween is more easily removed or wicked from inner volume 80. By interposing the air wick 44 along the entire surface of sleeve 40, up to skirt juncture 62 between skirt 42 and the sleeve 40 as shown, pockets of isolated air are avoided in envelope 59 so that the full retention force of the created vacuum extends along the entire outer surface 58 of sleeve 40 such that socket 46 and residual limb 91 are continuously drawn together. The retention of a vacuum attraction between socket 46 and limb 91 allows socket 46 to be of a substantially reduced size over conventional sockets and permits, in many cases, the disposal of bulky suspending straps.

As will be apparent to one skilled in the art, various modifications can be made within the scope of the aforesaid description. Such modifications being within the ability of one skilled in the art to form a part of the present invention and are embraced by the claims below. For example, air wicking, that ensures air permeation over the entire surface area 58 of sleeve 40, is currently satisfied through the utilization of a sock placed over sleeve 40. However, as briefly discussed above the inventor envisions that other structures may be employed to promote air permeation and avoid the creation of air pockets over the surface area of sleeve 40. Surface texture and molded structures in the surface 58 of sleeve 40 may be employed to promote air permeation across surface 58, such as vertical ridges 53 shown in FIG. 4, inset 55. Further, intervening substances, such as granularized powders, might also be employed to promote air permeation.

Having set forth the nature of the present invention, what is claim is:

1. An apparatus for attaching a prosthetic to a residual limb, comprising:
   a. a gas impervious sleeve for surrounding a lower portion of said limb, said sleeve having an outer surface;
   b. a gas impervious circumferential skirt integrally joined with and depending downward from an upper portion of said sleeve, said skirt having an outer surface;
   c. means positioned between said sleeve and said skirt for permeation of air between said outer surface of said sleeve and said skirt;
   d. a prosthetic socket having an inner surface and an outer surface, wherein said socket is positioned over said sleeve and said skirt, and wherein said outer surface of said skirt bears against said inner surface of said socket such that a airtight seal is created between said socket and said sleeve; and,
   e. said socket including a vacuum port in a lower portion thereof, said port connected to a vacuum source;
   f. wherein said socket is adapted to fit over a residual limb selected from a group consisting of a residual limb above the knee, a residual limb below the knee, a residual limb above the elbow, and a residual limb below the elbow; and
   g. wherein said permeation means comprises a fabric sock adapted to slide over said sleeve.

2. The apparatus as recited in claim 1, wherein said apparatus further comprises a prosthetic limb depending from said socket.

3. The apparatus as recited in claim 2, further comprising an upper margin on said sleeve and wherein said skirt attaches to said sleeve below said margin, and wherein said juncture between said skirt and said sleeve forms an inverted "V" shape.

4. An apparatus for attaching a prosthetic to a residual limb, comprising:
   a. a gas impervious sleeve for surrounding a lower portion of said limb, said sleeve having an outer surface;
   b. a gas impervious circumferential skirt integrally joined with and depending downward from an upper portion of said sleeve, said skirt having an outer surface.
   c. means positioned between said sleeve and said skirt for permeation of air between said outer surface of said sleeve and said skirt;
   d. a prosthetic socket having an inner surface and an outer surface, wherein said socket is positioned over said sleeve and said skirt, and wherein said outer surface of said skirt bears against said inner surface of said socket such that a airtight seal is created between said socket and said sleeve; and,
   e. said socket including a vacuum port in a lower portion thereof, said port connected to a vacuum source; and,
   f. wherein said permeation means comprises a fabric sock adapted to slide over said sleeve.

5. An apparatus for attaching a prosthetic to a residual limb, comprising:
   a. means for surrounding a lower portion of said limb with material, said material means having an outer surface and being gas impervious;
   b. means for gas imperviously sealing an upper circumferential portion of said material means;
   c. a fabric sock positioned between said material means and said sealing means for permeating air between said outer surface of said material means and said sealing means, wherein said sock is adapted to slide over said material means;

d. a prosthetic socket positioned over said material means and said sealing means, wherein an exterior surface of said sealing means bears against an interior surface of said socket such that an airtight seal is created between said socket and material means;

e. said socket also including means for connecting an interior of said socket with an exterior vacuum source; and f. wherein said socket is adapted to fit over a residual limb selected from a group consisting of a residual limb above the knee, a residual limb below the knee, a residual limb above the elbow, and a residual limb below the elbow.

6. The apparatus as recited in claim 5, wherein said apparatus further comprises a prosthetic limb depending from said socket.

7. The apparatus as recited in claim 6, further comprising an upper margin on said material means and wherein said sealing means attaches to said material means below said margin, and wherein said juncture between said sealing means and said material means forms an inverted "V" shape.

8. A system for attaching a prosthetic socket to a residual limb comprising:

a. a first gas impermeable pliable sleeve, and b. a second gas impermeable pliable sleeve concentrically positioned about the first sleeve and sealingly joined into the first sleeve such that said first and second sleeves form a unitary gas impermeable whole, wherein the second sleeve is configured for bearing against an interior surface of the prosthetic socket and forming a sealed chamber contained between the residual limb and the socket, and wherein the prosthetic socket is coupled to the first sleeve; and, c. an air permeable fabric positioned between the first sleeve and the second sleeve.

9. A system for attaching a prosthesis to a residual limb comprising:

a. a first gas impermeable pliable sleeve, and b. a second gas impermeable pliable sleeve concentrically positioned about the first sleeve, the second sleeve having a free lower margin and an upper margin integrally joined to the first sleeve such that said first and second sleeves form a unitary gas impermeable whole; and, c. a fabric, air permeable sock fitted over a lower end of the first sleeve and positioned between the first sleeve and the second sleeve.

10. A system for attaching a prosthesis to a residual limb comprising:

a. a first gas impermeable pliable sleeve, and b. a second gas impermeable pliable sleeve concentrically positioned about the first sleeve, the second sleeve having a free lower margin and an upper margin integrally joined to the first sleeve such that said first and second sleeves form a unitary gas impermeable whole; and, c. a prosthetic socket coupled to the first sleeve; and, d. a fabric sock positioned over a lower end of the first sleeve and between the first sleeve and the second sleeve.

11. A system for attaching a prosthesis to a residual limb comprising:

a. a pair of concentrically arranged, gas impermeable pliable sleeves, including an inner sleeve and an outer sleeve, each sleeve joined to the other such that said joined sleeves form a unitary gas impermeable whole, b. a prosthetic socket coupled to the pair of sleeves and conforming to the shape of a residual limb selected from a group consisting of a leg above the knee and a leg below the knee;

c. a chamber formed between the socket and the inner sleeve, wherein the outer sleeve and the interior surface of the socket cooperate such that the exterior surface of said outer sleeve bears against the interior surface of said socket to seal the chamber; and, d. further comprising an air permeable material positioned over a lower end of the inner sleeve and between the inner sleeve and the outer sleeve.

12. A method of attaching a prosthesis to a residual limb utilizing a system comprising:

a. a gas impervious sleeve for surrounding a lower portion of said limb, said sleeve having an outer surface;

b. a gas impervious circumferential skirt integrally joined with and depending downward from an upper portion of said sleeve, said skirt having an outer surface;

c. means positioned between said sleeve and said skirt for permeation of air between said outer surface of said sleeve and said skirt;

d. a prosthetic socket having an inner surface and an outer surface, wherein said socket is positioned over said sleeve and said skirt, and wherein said outer surface of said skirt bears against said inner surface of said socket such that a airtight seal is created between said socket and said sleeve; and, e. said socket including a vacuum port in a lower portion thereof, said port connected to a vacuum source;

the steps comprising:

a. placing the sleeve having the circumferential skirt depending downward from the upper portion of said sleeve about the residual limb;

b. positioning the means for allowing the permeation of air between an outer service of said sleeve and an inner surface of said skirt to flow therefrom;

c. inserting the sleeve, the permeation means, and the skirt into the socket conforming to the shape of the residual limb;

d. forming a continuous seal between the skirt and an interior surface of the socket such that a sealed chamber is formed within said socket;

e. evacuating air present in the socket through an expulsion port or said vacuum port; and, f. creating a vacuum within the chamber sufficient to maintain the socket coupled to and suspended from the residual limb.

13. The method according to claim 12 wherein said step of positioning said permeation means comprises elevating said skirt above an upper edge of said skirt, donning a sock over said sleeve such that a substantial portion of said sock extends toward said upper edge, and pulling said skirt down over said sock such that said sock separates the sleeve from the skirt.

14. The method according to claim 13 wherein said step of evacuating air from said socket comprises forcing air out of said expulsion port by inserting said residual limb into said socket and wherein said expulsion port is configured to only allow air to flow out of said socket.

15. The method according to claim 14 wherein said step of creating a vacuum within said chamber comprises attaching an air hose to the chamber and evacuating the air with a vacuum pump.

16. The method according to claim 15 further comprising removing air contained between the sleeve and the skirt by means of wicking air via said permeation means.

17. The method according to claim 13 further comprising removing air contained between the sleeve and the skirt by means of wicking air via said permeation means.

18. The method according to claim 13 further comprising pulling air from the chamber through a vacuum pump coupled to an opening in the socket.

19. The method according to claim 13 wherein the residual limb is a leg below the knee.

20. The method according to claim 13 wherein the residual limb is a leg above the knee.

21. A method of attaching a prosthesis to a residual limb utilizing a system comprising:
   a. a gas impervious sleeve for surrounding a lower portion of said limb, said sleeve having an outer surface;
   b. a gas impervious circumferential skirt integrally joined with and depending downward from an upper portion of said sleeve, said skirt having an outer surface;
   c. means positioned between said sleeve and said skirt for permeation of air between said outer surface of said sleeve and said skirt, said means comprising an air permeable sock;
   d. a prosthetic socket having an inner surface and an outer surface, wherein said socket is positioned over said sleeve and said skirt, and wherein said outer surface of said skirt bears against said inner surface of said socket such that a airtight seal is created between said socket and said sleeve; and,
   e. said socket including a vacuum port in a lower portion thereof, said port connected to a vacuum source;

the steps comprising:
   a. placing the prosthetic sleeve having the circumferential skirt depending downward from the upper portion of said sleeve about the residual limb,
   b. placing the air permeable sock over the residual limb and sleeve between said skirt and said sleeve,
   c. inserting the residual limb, sleeve, skirt, and sock into the socket conforming to the shape of the residual limb,
   d. forming a continuous seal between the sleeve and an interior surface of the socket,
   e. evacuating air from the socket, and
   f. forming a vacuum within the socket such that a sealed chamber is formed within said socket due to the cooperation of said interior surface of said socket and the exterior surface of said skirt.

22. The method according to claim 21 wherein said step of evacuating air further comprising removing air contained between the sleeve and the skirt by means of wicking air via said sock.

23. The method according to claim 21 wherein said step "a" further comprises selecting said residual limb from the group consisting of a residual limb above the knee and a residual limb below the knee.

* * * * *